United States Patent
Link et al.

(10) Patent No.: US 7,527,629 B2
(45) Date of Patent: May 5, 2009

(54) INSTRUMENT SET FOR FITTING AN INTERVERTEBRAL JOINT PROSTHESIS

(75) Inventors: Helmut D. Link, Hamburg (DE); Arnold Keller, Kayhude (DE); Paul C. McAfee, Baltimore, MD (US)

(73) Assignee: Cervitech, Inc., Rockaway, NJ (US)

( * ) Notice: Subject to any disclaimer, the term of this patent is extended or adjusted under 35 U.S.C. 154(b) by 394 days.

(21) Appl. No.: 10/731,432

(22) Filed: Dec. 10, 2003

(65) Prior Publication Data

US 2004/0177494 A1 Sep. 16, 2004

Related U.S. Application Data

(63) Continuation-in-part of application No. 10/357,516, filed on Feb. 4, 2003, now abandoned.

(30) Foreign Application Priority Data

Mar. 12, 2002 (EP) .................... 02005629

(51) Int. Cl.
*A61F 5/00* (2006.01)
(52) U.S. Cl. ....................................... 606/87
(58) Field of Classification Search .............. 606/61, 606/79, 80, 86, 87, 96, 90, 97, 99
See application file for complete search history.

(56) References Cited

U.S. PATENT DOCUMENTS

| | | | |
|---|---|---|---|
| 4,289,123 A | 9/1981 | Dunn | |
| 4,672,957 A | 6/1987 | Hourahane | |
| 4,820,305 A | 4/1989 | Harms et al. | |
| 4,892,545 A | 1/1990 | Day et al. | |
| 4,936,848 A | 6/1990 | Bagby | |
| 5,059,194 A | 10/1991 | Michelson | |
| 5,397,364 A | 3/1995 | Kozak et al. | |
| 5,484,437 A | 1/1996 | Michelson | |
| 5,534,005 A | 7/1996 | Tokish et al. | |
| 5,591,235 A | 1/1997 | Kuslich | |
| 5,735,856 A | 4/1998 | McCue et al. | |

(Continued)

FOREIGN PATENT DOCUMENTS

DE 9217816 U1 6/1994

(Continued)

OTHER PUBLICATIONS

Search protocol dated Mar. 30, 2005 showing the family information of WO 2004080333.

(Continued)

*Primary Examiner*—Eduardo C Robert
*Assistant Examiner*—Richard Shaffer
(74) *Attorney, Agent, or Firm*—Morrison & Foerster, LLP

(57) ABSTRACT

Instrument set for fitting an intervertebral prosthesis, comprising a guide device (4) for an instrument or a prosthesis part, which guide device (4) is to be secured on at least one vertebral body (2). To be able to attach the guide device (4) precisely on the vertebral bodies despite the difficult operating conditions, an adjustment instrument (10) is provided which positions the guide device when this is being arranged on the vertebral body (2). This adjustment instrument (10) expediently comprises an intervertebral plate (11) which is fitted into the intervertebral space so as to be positioned exactly in relation to the vertebral bodies.

1 Claim, 9 Drawing Sheets

U.S. PATENT DOCUMENTS

Figure 1:
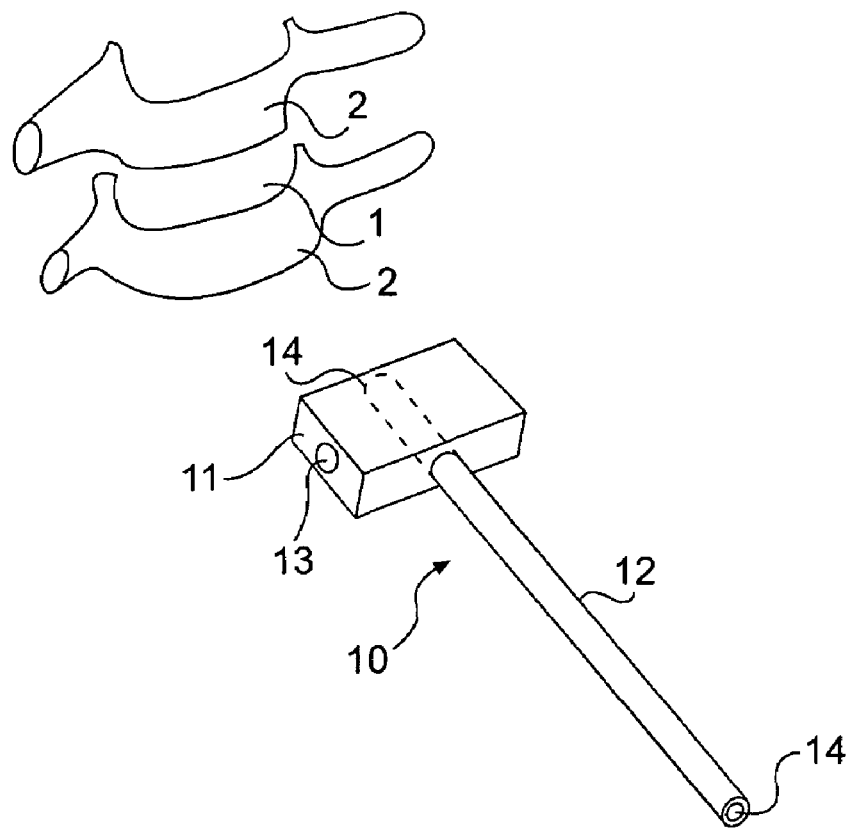

| | | | |
|---|---|---|---|
| 5,772,661 | A | 6/1998 | Michelson |
| 5,797,909 | A | 8/1998 | Michelson |
| 6,063,088 | A * | 5/2000 | Winslow .................... 606/61 |
| 6,080,155 | A | 6/2000 | Michelson |
| 6,083,228 | A | 7/2000 | Michelson |
| 6,086,595 | A | 7/2000 | Yonemura et al. |
| 6,096,038 | A | 8/2000 | Michelson |
| 6,156,040 | A | 12/2000 | Yonemura et al. |
| 6,159,214 | A | 12/2000 | Michelson |
| 6,224,599 | B1 | 5/2001 | Baynham et al. |
| 6,224,607 | B1 | 5/2001 | Michelson |
| 6,270,498 | B1 | 8/2001 | Michelson |
| 6,277,122 | B1 | 8/2001 | McGahan et al. |
| 6,296,647 | B1 | 10/2001 | Robioneck et al. |
| 6,332,887 | B1 | 12/2001 | Knox |
| 6,440,139 | B2 | 8/2002 | Michelson |
| 6,447,512 | B1 | 9/2002 | Landry et al. |
| 6,447,545 | B1 | 9/2002 | Bagby |
| 6,517,544 | B1 | 2/2003 | Michelson |
| 6,540,735 | B1 | 4/2003 | Ashby et al. |
| 6,562,041 | B1 | 5/2003 | Yonemura et al. |
| 6,740,087 | B2 | 5/2004 | Knox |
| 6,761,723 | B2 * | 7/2004 | Buttermann et al. .......... 606/79 |
| 7,025,787 | B2 * | 4/2006 | Bryan et al. ............. 623/17.16 |
| 2001/0000532 | A1 | 4/2001 | Michelson |
| 2001/0010001 | A1 | 7/2001 | Michelson |
| 2001/0010002 | A1 | 7/2001 | Michelson |
| 2002/0026191 | A1 | 2/2002 | Dixon et al. |
| 2002/0058944 | A1 | 5/2002 | Michelson |
| 2002/0068941 | A1 | 6/2002 | Hanson et al. |
| 2002/0091390 | A1 | 7/2002 | Michelson |
| 2002/0091392 | A1 | 7/2002 | Michelson |
| 2002/0138079 | A1 | 9/2002 | Cohen |
| 2003/0028197 | A1 | 2/2003 | Hanson et al. |
| 2003/0032962 | A1 * | 2/2003 | McGahan et al. ............. 606/80 |
| 2003/0045938 | A1 | 3/2003 | Kohrs et al. |
| 2003/0135217 | A1 * | 7/2003 | Buttermann et al. .......... 606/79 |
| 2003/0135277 | A1 | 7/2003 | Bryan et al. |
| 2003/0220689 | A1 | 11/2003 | Ritland et al. |
| 2004/0092943 | A1 * | 5/2004 | Buttermann et al. .......... 606/87 |
| 2004/0156168 | A1 | 8/2004 | LeVasseur et al. |
| 2004/0176772 | A1 | 9/2004 | Zubok et al. |
| 2004/0176843 | A1 | 9/2004 | Zubok et al. |
| 2004/0186482 | A1 | 9/2004 | Kolb et al. |
| 2004/0193272 | A1 | 9/2004 | Zubok et al. |
| 2004/0220590 | A1 | 11/2004 | Zubok et al. |
| 2004/0236342 | A1 | 11/2004 | Ferree et al. |
| 2005/0015092 | A1 | 1/2005 | Rathbun et al. |

FOREIGN PATENT DOCUMENTS

| | | |
|---|---|---|
| DE | 29916078 U | 11/1999 |
| DE | 19836498 A1 | 2/2000 |
| DE | 201 10 393 U1 | 9/2001 |
| DE | 201 10 402 U1 | 9/2001 |
| DE | 20111479 U1 | 11/2001 |
| DE | 102 26 496 | 1/2003 |
| DE | 10134505 A1 | 1/2003 |
| DE | 202004014768 U1 | 12/2004 |
| EP | 0333990 A2 | 9/1989 |
| FR | 2737656 | 2/1997 |
| WO | WO-97/38635 | 10/1997 |
| WO | WO 00/53127 A1 | 9/2000 |
| WO | WO-01/13807 A2 | 3/2001 |
| WO | WO 01/49188 A1 | 7/2001 |
| WO | WO-01/62166 A2 | 8/2001 |
| WO | WO-03/075774 A | 9/2003 |
| WO | WO-2004/089258 A1 | 10/2004 |

OTHER PUBLICATIONS

Search Report dated Mar. 18, 2005.
International Search Report dated Mar. 22, 2005.
International Search Report mailed Jul. 17, 2003, directed to related foreign application.
International Search Report dated Jun. 23, 2005 directed to counterpart PCT/EP2004/013346 (8 pages).

* cited by examiner

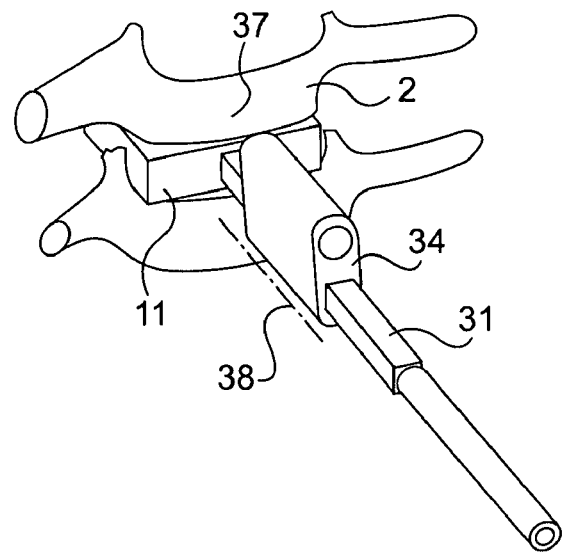
FIG. 7
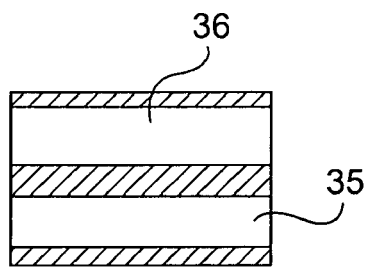 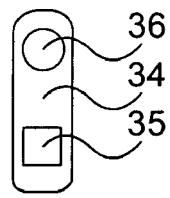 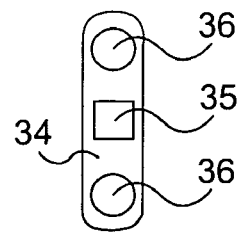
FIG. 8   FIG. 9A   FIG. 9B
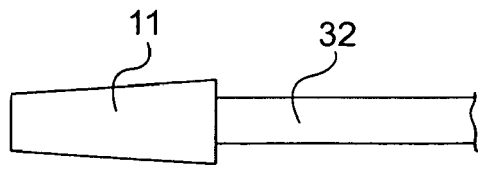
FIG. 10

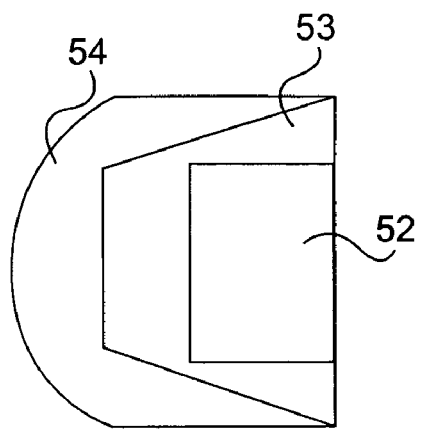
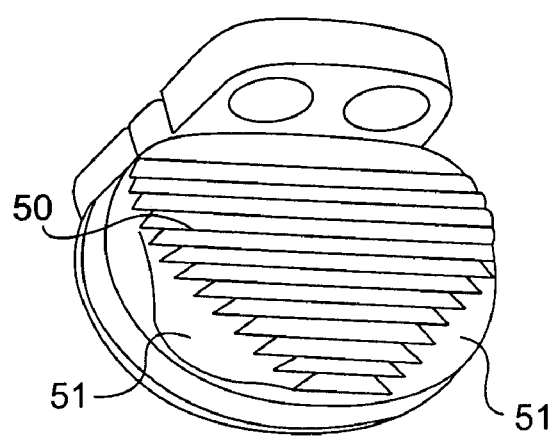
FIG. 21  FIG. 22
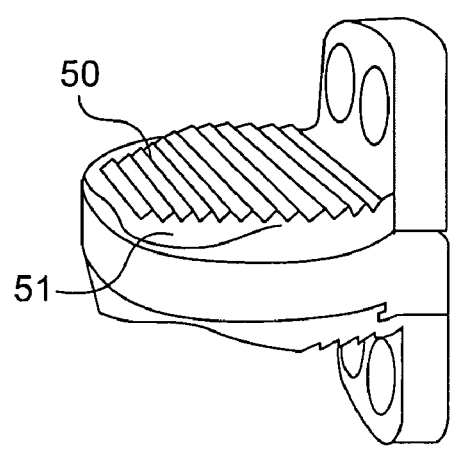
FIG. 23

INSTRUMENT SET FOR FITTING AN INTERVERTEBRAL JOINT PROSTHESIS

REFERENCE TO RELATED APPLICATIONS

This application is a continuation-in-part of Ser. No. 10/357,516, filed Feb. 4, 2003, now abandoned which claims priority from European Application No. 02 005 628.7, filed Mar. 12, 2002.

When fitting an intervertebral joint prosthesis as a replacement for an intervertebral disk, the operating surgeon is working in an operating site which is very difficult to see and which is in immediate proximity to important nerve paths and blood vessels. This applies in particular to the area of the cervical spine, because here the dimensions of the vertebrae are very small and there is particularly little distance to sensitive adjoining areas. Therefore, in the case of instruments which pose a particular risk of damage or which have to be inserted with particular precision, it is sought to limit their freedom of movement to the necessary range by means of suitable instruments. In doing so, however, visual monitoring must as far as possible remain unaffected.

In order to fit so-called cages which serve for fusion of the vertebral bodies and whose cross-sectional dimensions are much smaller than those of an intervertebral prosthesis, it is known (U.S. Pat. No. 5,772,661) for the cages to be fitted and for the matching vertebral surfaces to be worked via a protective sleeve. The latter is provided at its front end with spikes which penetrate into the vertebral bodies concerned in order to secure their relative position. This assumes that the protective sleeve itself is precisely positioned, the vertebral bodies having first been brought to the desired spacing. To do this, a needle is used which is introduced into the intervertebral disk with the same axis as the intended position of the protective sleeve. An intermediate sleeve is pushed over the needle, this intermediate sleeve having, at its front end, distractor blades which penetrate into the intervertebral space in order to spread the vertebral bodies apart. The protective sleeve is then pushed over this intermediate sleeve. As soon as it has reached the vertebral bodies and these are fixed by the spikes located on the protective sleeve, the needle and the intermediate sleeve can be removed. For fitting an intervertebral prosthesis, such an arrangement is unsuitable for several reasons. On the one hand, because of the larger dimensions of an intervertebral prosthesis, the protective sleeve would have to be very substantial and would be able to be accommodated only with difficulty in the confined operating site. On the other hand, it is difficult to imagine an intervertebral prosthesis being precisely oriented and positioned by way of such a protective sleeve. Because of its size, the protective sleeve would also greatly obstruct the view of the site.

In order to fit cages, another type of instrument is also known (U.S. Pat. No. 6,159,214) in which a milling block is connected to a distractor blade before being arranged on the vertebral bodies, said distractor blade being pushed into the intervertebral space in order to spread the vertebrae apart. The distractor block can then be firmly connected by means of pins to the vertebral bodies and the distractor blade can be removed. This has the disadvantage that the milling block obstructs the operating surgeon's view of the distractor blade when the distractor blade is pushed into the intervertebral space. It is therefore difficult to precisely position the known device. When fitting cages, this can be tolerated, because the milling block is small and the positioning accuracy demanded of the cage is not high. For fitting intervertebral joint prostheses, however, such an arrangement cannot be used because the obstruction of the operating surgeon's view is too great and a very high degree of precision is demanded.

The abovementioned distractor blades also have the disadvantage that they may cut into the vertebral bodies and then do not provide satisfactory distraction. To avoid this disadvantage, it has also been disclosed (U.S. Pat. No. 6,224,599) to drive a pair of distractor blades into the intervertebral space together with a relatively wide distractor wedge arranged between them and permitting a greater surface area for distraction of the vertebral bodies. After these have been driven in, the wedge is removed. Only the distractor blades remain in the intervertebral space. An instrument permitting working of the intervertebral space and insertion of two cages is then connected to these distractor blades. The distractor blades are removed again thereafter. This instrument is not suitable for inserting an intervertebral prosthesis.

In another known instrument for inserting cages (U.S. Pat. No. 6,277,122), a distractor plate is first introduced into the intervertebral space, said distractor plate being provided with longitudinal ribs to ensure that it cannot move laterally while being driven in. This also makes subsequent correction of the position impossible. This can be tolerated when using cages, because these do not have to be fitted with a high degree of precision. The known instrument is not suitable for inserting an intervertebral prosthesis. This is also due to the fact that, before insertion of the cages, the plate is replaced by a guide sleeve which, although permitting the insertion of the cage, is not suitable for an intervertebral prosthesis.

In another known instrument for inserting cages (US-A-2001/0031968; WO 01/13807), it is known first to push a plate into the intervertebral space, which plate serves to distract the vertebral bodies enclosing the intervertebral space. It is in two parts. After it has been pushed into the intervertebral space, one part is removed and replaced by a cage. The other part of the plate can then also be removed and replaced by a cage. This instrument is suitable only in cases where two cages are provided which are to be arranged next to one another in the intervertebral space. It is not suitable for insertion of an intervertebral prosthesis.

Instruments for inserting intervertebral prostheses into the lumbar spine are known (DE-U-299 16 078, EP-A-0 333 990, FR-A-2737656) in which the cover plates of a prosthesis are first driven into the intervertebral space and spread open, and then the prosthesis core is pushed in between them. In this case, working of the vertebral surfaces can generally be dispensed with. The insertion instruments are relatively large, but this can be tolerated in the area of the lumbar spine. The intervertebral spaces in the area of the cervical spine are so narrow that space for receiving the prostheses must be created by reaming out the adjacent vertebral bodies. In doing so, the access space is so narrow and, because of the proximity of vital organs, so sensitive that large instruments cannot be used.

The object of the invention is to make available an instrument set for preparing the cervical spine for fitting an intervertebral joint prosthesis, said instrument set permitting a high degree of precision and the best possible visual control.

The instrument set as claimed in claim 1 has a guide device which is connected to the vertebral bodies concerned. It can be used to fix them in the desired relative position. It can also be used for guiding a tool for working the surfaces of the vertebral bodies. To arrange it with precision, an adjustment instrument is used which comprises an intervertebral plate. After the intervertebral disk and possibly the ventral protrusions of the upper vertebral body have been removed, it is fitted into the intervertebral space and precisely positioned. After it has been positioned, it provides an exact indication of the position of the vertebral body surfaces between which the prosthesis is to be placed. It also ensures that the vertebral bodies are at the predetermined spacing from one another. In this way, a measure for the positioning of the guide device is obtained so that, with the aid of the adjustment instrument, the guide device can be positioned exactly, i.e. with the same precision as the adjustment instrument itself. The relative position of the vertebral bodies is thus ensured, as is the positional precision of the machining tools guided by the guide device.

Adjustment surfaces are provided on the intervertebral plate and cooperate with the guide device. It is particularly advantageous if these adjustment surfaces are in the form of an adjustment rod which projects in the ventral direction from the intervertebral plate. This allows the operating surgeon to join together the cooperating adjustment surfaces of the rod and of the guide device in a front, clearly viewable part of the operating site, instead of in the concealed depths. The guide device is then guided along the adjustment rod into the depths of the operating site until it reaches the vertebrae. In a possible first embodiment of the invention, it is then secured to the vertebrae. This securing takes place as long as the guide device is still positioned by the adjustment instrument. Thereafter, it is removed.

To facilitate the positioning of the adjustment instrument, the intervertebral plate is expediently chosen such that it has approximately the same shape and size as the natural intervertebral space or such that its extent is only slightly smaller than that of the intervertebral space. This makes it easier to position since, because of its shape, it automatically adopts a position centered with respect to the intervertebral space and in the same orientation. It can also be provided with X-ray control markers for more accurate positioning. It is held in the intended position by the tensioning generated by the natural ligaments between the vertebral bodies. This tensioning depends on the thickness of the intervertebral plate. A sufficient tensioning is in any case present if this thickness is about as great as the thickness of the intended prosthesis. To ensure that its position can still be corrected later, its surface is essentially smooth, i.e. without elevations which, by sinking into the bone surface or cartilage surface, make relative movement parallel to the surface direction difficult.

In the first embodiment, the guide device has an opening through which the machining later takes place with the tool. The adjustment instrument is removed through this opening. It must therefore be at least as large as the intervertebral plate. So that the adjustment rod does not also have to have the same cross section in order to be able to cooperate with the boundary surfaces of the opening acting as adjustment surfaces, an intermediate adjustment piece is expediently provided. This intermediate adjustment piece has, on the one hand, surfaces which slide with an exact fit on the adjustment surfaces of the adjustment instrument (i.e. on the adjustment rod) and, on the other hand, surfaces which cooperate with the adjustment surfaces of the securing device. These are expediently formed by the opening in the guide device. Furthermore, a gauge can be provided which can be applied to the guide device, inside the opening thereof, and which forms the guide surfaces for the machining tools.

In another embodiment of the invention, the guide device is further held by the adjustment instrument. The working of the vertebral bodies with the aid of the guide device then takes place as long as this is still connected to the adjustment instrument and held by the latter in the exact position.

In both embodiments of the invention, a method for implanting an intervertebral prosthesis can be carried out wherein, in a first step, the intervertebral disk is removed; in a second step an intervertebral plate having a surface area slightly smaller than the surface area of the intervertebral space and having X-ray markers suitable for X-ray control is introduced into the intervertebral space and positioned under X-ray control; in a third step a guide device is applied with a matching fit to an adjustment rod projecting from the intervertebral plate and is applied against the vertebral bodies; in a further step the vertebral bodies are worked with the aid of the guide device, and, finally, the intervertebral prosthesis is fitted.

The invention further relates to an instrument set for fitting an intervertebral prosthesis into an intervertebral space between two vertebral bodies, which instrument set comprises a device for guiding at least one tool for working a vertebral body, and an adjustment instrument which is used for adjusting the guide device and which has an intervertebral plate to be fitted into the intervertebral space and, projecting from this plate, an adjustment rod cooperating with the guide device. In this case, the intervertebral plate or the adjustment rod has a marking detectable in an AP X-ray beam path, making it possible to position the intervertebral plate exactly centrally in relation to the median plane of the vertebral bodies. The abbreviation AP means antero-posterior and here designates an X-ray beam path extending in the antero-posterior direction. To permit the positioning of the intervertebral plate even when it has already been driven into the intervertebral space, in this case its surface should also be sufficiently smooth so that a movement is still possible in particular perpendicular to the median plane. For an X-ray beam path extending in the transverse direction, the adjustment plate can also have X-ray markers to permit exact positioning in the AP direction. The X-ray marker can simply be formed by the surface of the radiopaque intervertebral plate or adjustment rod.

In the embodiment of the invention in which the guide device is held steady by the adjustment instrument, it is expedient for the adjustment rod and the guide device to have interacting surfaces shaped so as to complement one another to give a non-rotational fit, so that the guide device cannot turn in relation to the adjustment rod. The guide device is expediently a drill gauge for two drill axes arranged in parallel in the median plane above and below the adjustment rod. For example, two drill gauges can be arranged on a hub of the guide device surrounding the adjustment rod. In a variant embodiment, only one drill gauge is arranged on the hub surrounding the adjustment rod, and the interacting surfaces of the hub and of the adjustment rod fit together in two positions offset 1800 in relation to one another. In the first position, the guide device is used to make a hole in a first of the two vertebral bodies and, if appropriate, to anchor a screw pin therein. The guide device is then pulled back along the adjustment rod, turned through 180°, and pushed forward again to permit the same working of the other vertebral body.

If the intervertebral disk between two cervical vertebrae is so badly damaged that it has to be replaced by a prosthesis, the vertebral bodies have generally moved so close to one another that the natural kyphosis (curvature of the cervical spine with the center of curvature lying dorsally) is reduced. In these cases, it is not enough to perform distraction of the vertebral bodies before fitting the intervertebral prosthesis, and instead it is expedient to restore the natural kyphosis. According to the invention, this is achieved by the fact that the intervertebral plate is wedge-shaped, i.e. its thickness decreases from its ventral margin toward its distal margin. The instrument set can include intervertebral plates with different wedge angles.

The invention relates to an instrument set for fitting an intervertebral prosthesis into the intervertebral space between two vertebral bodies, which instrument set comprises an adjustment device consisting of an intervertebral plate positionable in the intervertebral space and of an adjustment rod projecting from the intervertebral plate, and a guide device having a hub which can be pushed onto the adjustment rod and which cooperates with the adjustment rod via complementary surfaces shaped to give a non-rotational fit, the guide device forming two guide axes located in the median plane below and above the adjustment rod and extending parallel to the latter.

The invention further relates to an instrument set for fitting an intervertebral prosthesis in the intervertebral space and between two vertebral bodies, which comprises a) an adjustment device consisting of an intervertebral plate and of an adjustment rod projecting from the latter,
b) a guide device which is supported loosely by the adjustment rod and which forms two guide axes lying in the median plane below and above the adjustment rod and parallel to the latter, these axes being intended for a cylindrical turning instrument,
c) two pins which can be introduced into the vertebral bodies parallel to one another by means of the turning instrument, and
d) a spreader instrument holding the pins parallel.

In this way, a method for fitting an intervertebral prosthesis into the intervertebral space between two vertebral bodies is made possible wherein, in a first step, the intervertebral disk is removed, in a second step the intervertebral plate of an adjustment instrument is positioned in the intervertebral space and secured therein, in a third step the hub of a guide device is pushed onto an adjustment rod, projecting from the intervertebral plate, in such a way that it defines two guide axes in the median plane above and below the adjustment rod and parallel thereto, in a fourth step two pins are introduced into the vertebrae in the direction of the guide axes, in a fifth step a spreading forceps is connected to the pins so that they are held parallel to one another, and in further steps the spacing of the intervertebral bodies is set, the guide device and the adjustment element are removed, the intervertebral space is worked, if so desired, and the intervertebral prosthesis is fitted.

Figure 2:
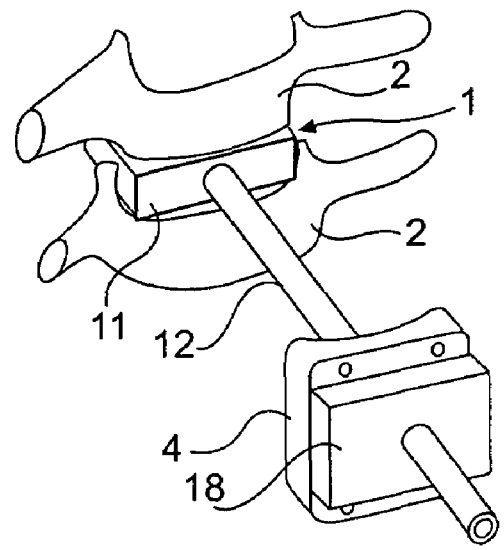
Figure 3:
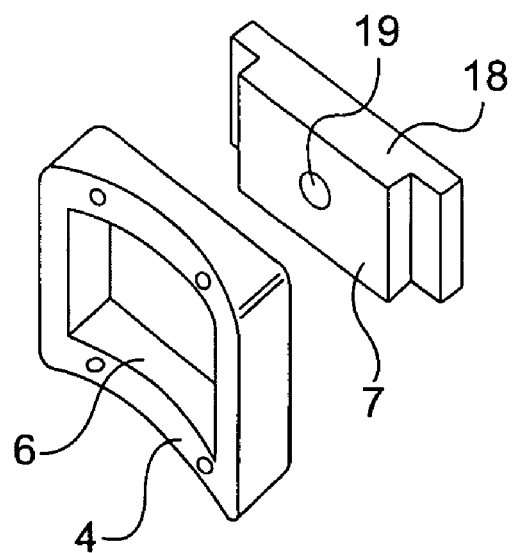
Figure 4:
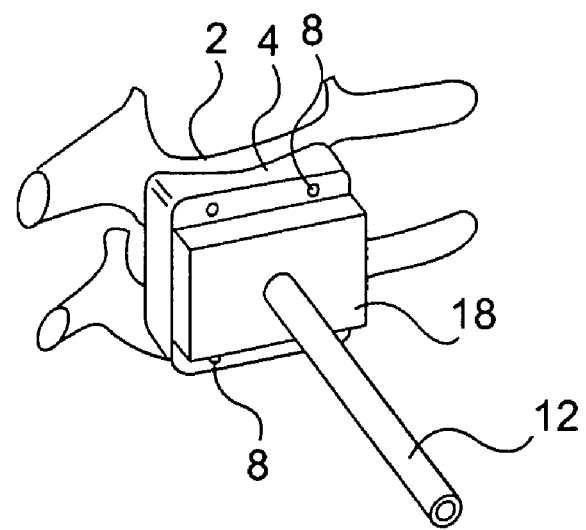
Figure 5:
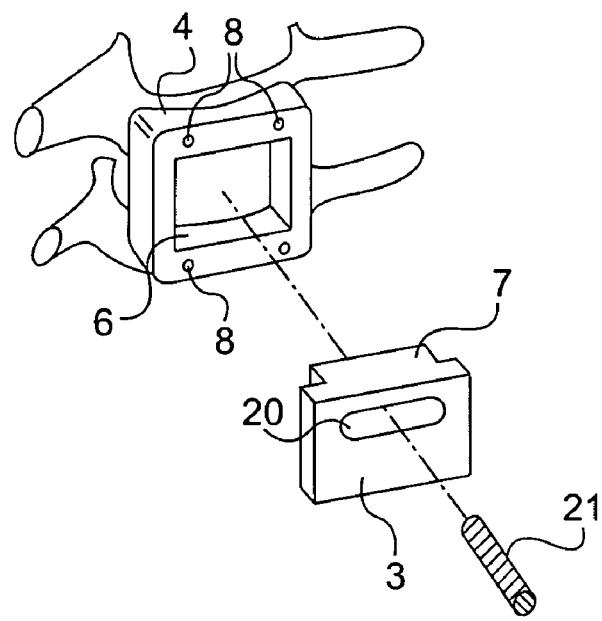
Figure 6:
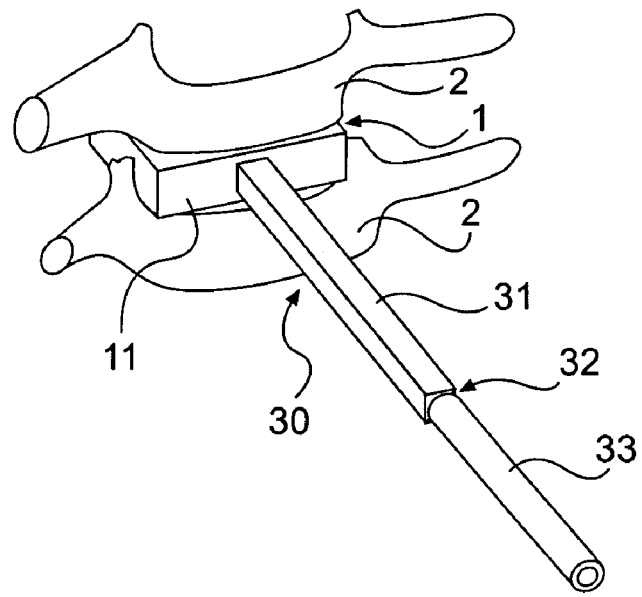
Figure 11:
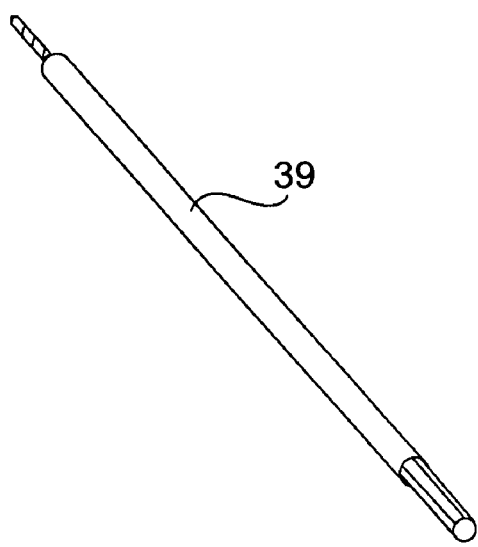
Figure 12:
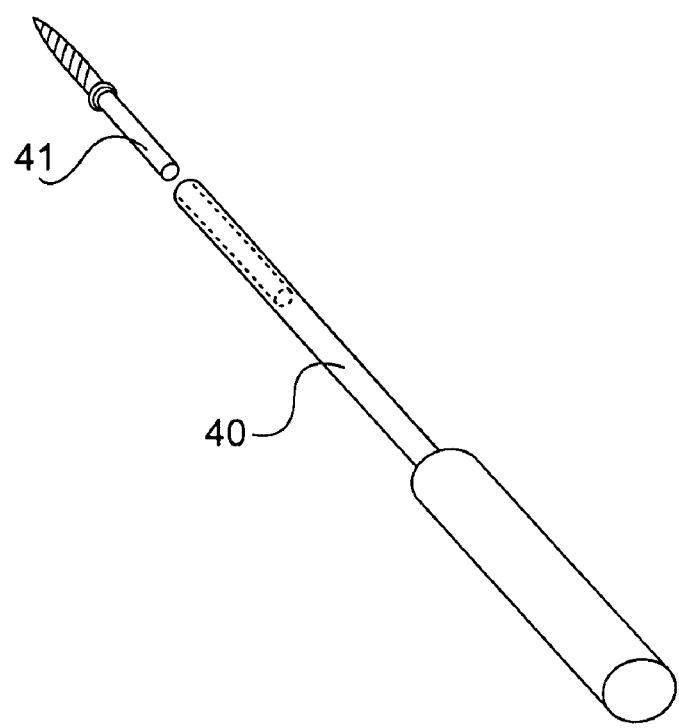
Figure 13:
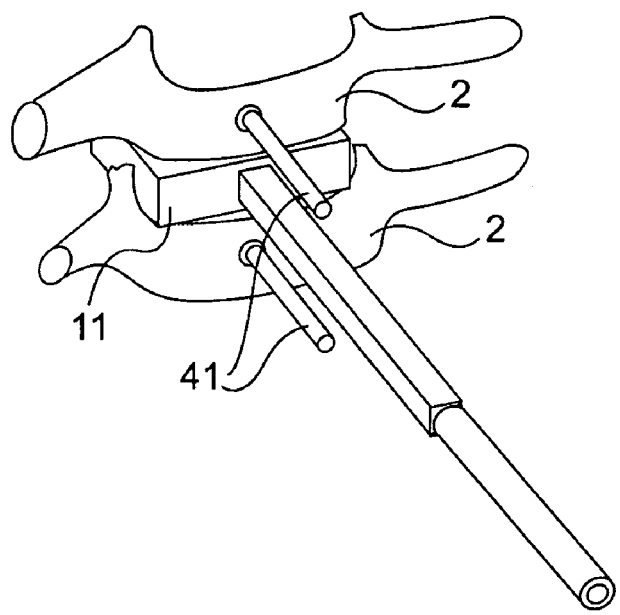
Figure 14:
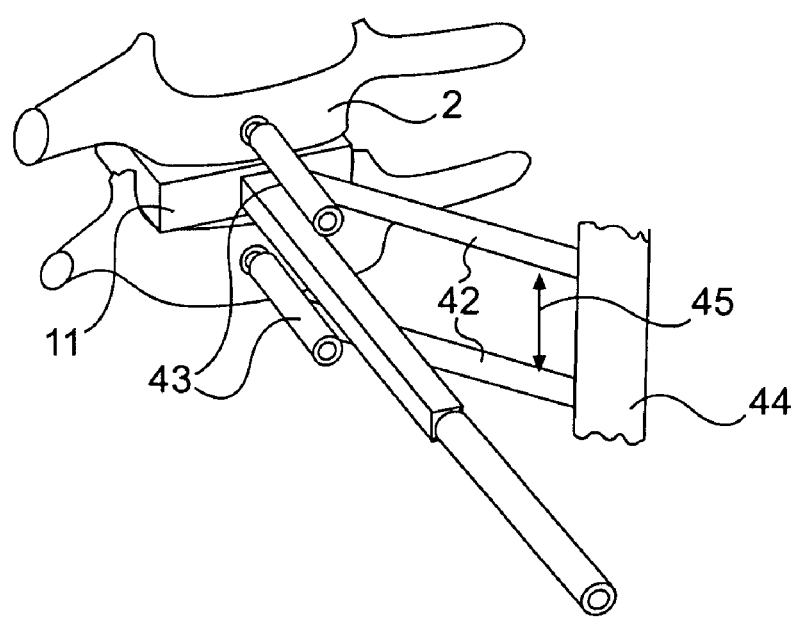
Figure 15:
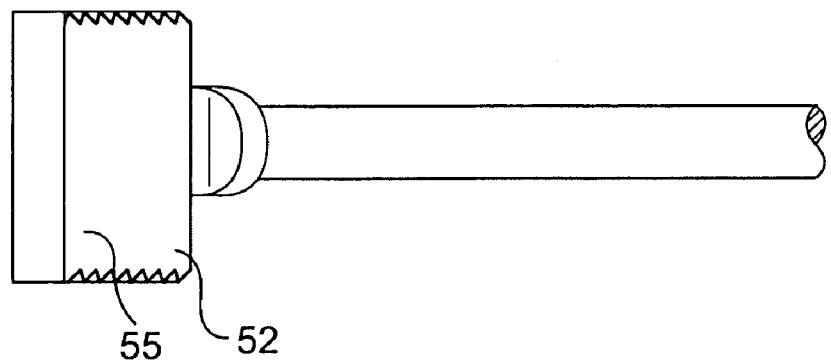
Figure 16:
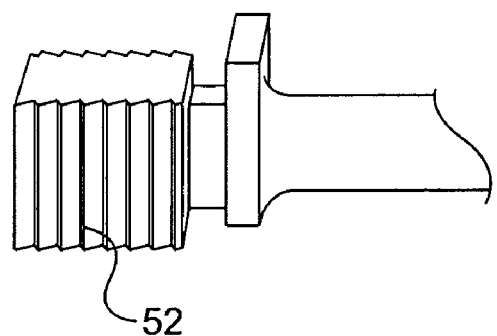
Figure 17:
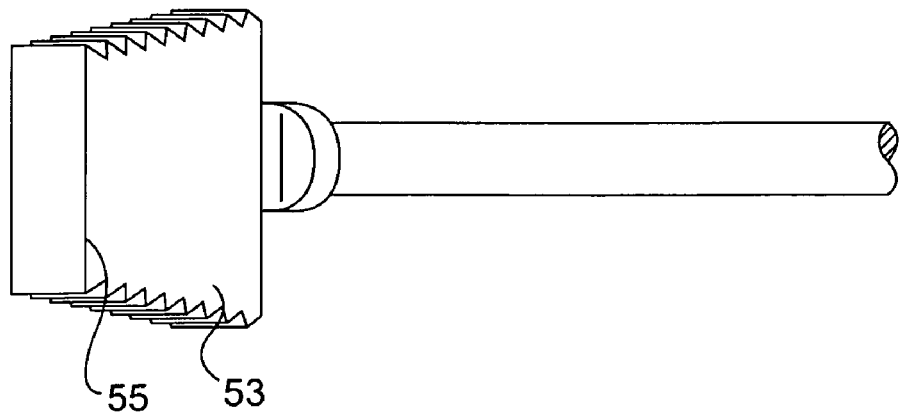
Figure 18:
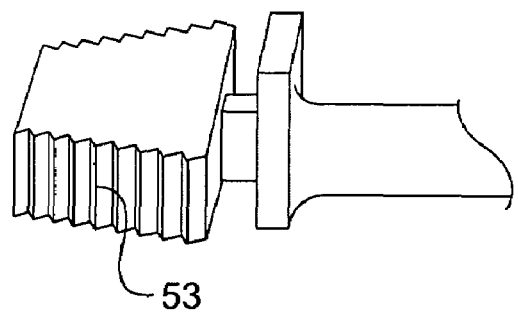
Figure 19:
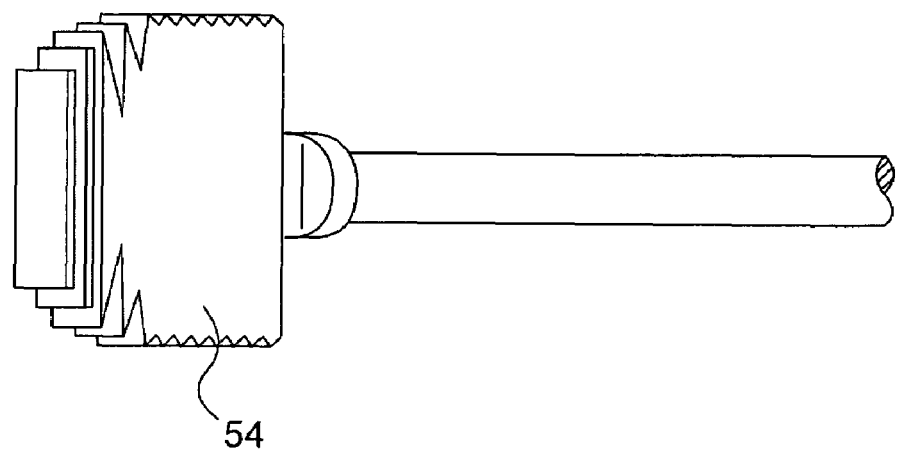
Figure 20:
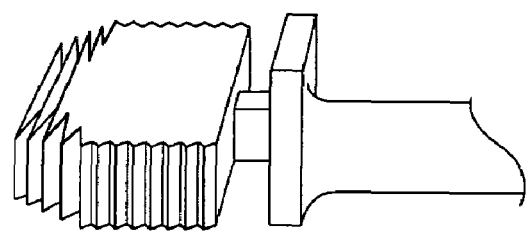

The invention is explained in more detail below with reference to the drawing, in which:

FIGS. 1-5 show a first embodiment, namely:

FIG. 1 a diagrammatic perspective enlarged view, obliquely from the ventral direction, of a pair of cervical vertebrae, with an adjustment instrument situated in front of them, FIG. 2 the same view with the adjustment instrument inserted, FIG. 3 the guide device with intermediate adjustment piece, FIG. 4 the view according to FIG. 1, with the adjustment instrument inserted and the guide device attached, FIG. 5 the view according to FIG. 1, without the adjustment instrument, with the guide device attached, and with milling gauge, FIGS. 6-14 show a second embodiment, namely:

FIG. 6 a view of the inserted adjustment instrument corresponding to FIG. 1,

FIG. 7 with a guide device pushed onto the adjustment rod,

FIG. 8 a cross-sectional view of the guide device embodiment,

FIG. 9a an end view of the guide device embodiment,

FIG. 9b an end view of an alternate guide device embodiment,

FIG. 10 a partial side view of the adjustment instrument,

FIG. 11 a drill to be used with the guide device,

FIG. 12 a screwdriver and screw pin to be used with the guide device,

FIG. 13 a view, corresponding to FIG. 6, with screw pins inserted into the vertebrae, and FIG. 14 a view, corresponding to FIG. 13, with a spreader instrument applied, FIGS. 15-23 show rasp tools for a specific prosthesis, namely:

FIGS. 15-20 a set of three different rasps,

FIG. 21 the contour of the rasps for comparison, and

FIGS. 22-23 the prosthesis for which the rasps are intended.

According to FIGS. 1-5, an intervertebral joint prosthesis is to be inserted into the intervertebral space 1 of the vertebral bodies 2. To do so, those faces of the vertebral bodies 2 facing one another have to be worked. Sensitive areas lie close by. To minimize the risks associated with the preparatory work, a machining gauge 3 is to be used which can be secured on the vertebral bodies 2 at a predetermined position. This is done using the guide device 4. The latter is frame-shaped with an opening 6 which is designed to match a projection 7 on the gauge 3. It is to be secured on the vertebral bodies 2 by means of pins 8. This has to be done with a high level of precision. By virtue of its frame shape, it is very flat, with the result that it does not impede visual monitoring and can also be used in a confined operating site.

For positioning it, the adjustment instrument 10 is provided. It comprises an intervertebral plate 11 and an adjustment rod 12 connected rigidly to the latter. The intervertebral plate 11 has a surface area which is slightly smaller than the surface area of the intervertebral space 1. Its thickness is generally not greater than that of an intervertebral joint prosthesis. It is at any rate of such a size that, after removal of the intervertebral disk, it can be fitted into the intervertebral space 1 and there is held securely in its assigned position by means of the natural tension prevailing between the vertebral bodies 2. It has a transverse bore 13, and an AP bore 14 which the guide rod 12 also passes through. These bores make it possible to position the intervertebral plate 11 exactly in the intervertebral space 1 under X-ray control. The adjustment rod 12 then has an exactly defined position in relation to the vertebral surfaces enclosing the intervertebral plate 11.

To be able to adjust the guide device 4 on the adjustment rod 12, the intermediate adjustment piece 18 is provided that, just like the milling gauge 3, has a projection 7 fitting into the opening 6. It has a bore 19 matching the external diameter of the adjustment rod 12. The parts are first joined together so that, by virtue of their friction or other suitable means of adhesion, they are connected sufficiently firmly to one another for manipulation. They are then placed with the bore 19 onto the rod 14 and can slide along the latter until the guide device 4 bears on the ventral faces of the vertebral bodies 2.

The fact that the guide device 4 sits on the adjustment rod 12 via the intermediate adjustment piece 18 guarantees that it has exactly the right height with respect to the vertebral end faces which delimit the intervertebral space 1. It is true that it can turn about the rod 12, but no real incorrect setting is possible in this respect. If one wishes also to reliably avoid this, the adjustment rod 12 and the associated opening 19 are not cylindrical in shape but instead prismatic, for example having a rectangular cross section.

As soon as the guide device 4 has reached the intended position on the vertebrae 2, as is shown in FIG. 4, it is secured to the vertebral bodies 2 by means of fine bone screws through its bores 8. The intermediate adjustment piece 18 and the intervertebral plate 11 can now be removed through the opening 6. This gives the situation shown in FIG. 5.

Any desired machining gauges 3 can now be fitted into the opening 6 of the guide device 4, these machining gauges 3 having cutouts 20 adapted to and guiding the machining tools respectively used. For example, the slit 20 shown in FIG. 5 can serve to guide a cylindrical milling cutter 21 which is used to work the prosthesis contact surface of the upper vertebral body 2. To machine the lower vertebral body, the machining gauge is turned through 180°.

After the machining of the vertebral bodies, the intervertebral space thus formed has the predetermined dimensions for receiving the prosthesis. The latter can now be fitted. The guide device can be removed beforehand (but does not need to be).

The second illustrative embodiment shown in FIGS. 6-14 uses an adjustment instrument 30 whose intervertebral plate 11 can be the same as the one described in the first example. It can be wedge-shaped in side view, as is shown in FIG. 10. The main difference from the first illustrative embodiment is that the adjustment rod 32 has a square cross section, at least in its area 31 near the intervertebral plate 11, while the portion 33 farther away from this is shown with a round cross section. The adjustment rod 32 is also designed in this case as a tube so as to be able to serve as an X-ray marker for an X-ray beam path extending in the AP direction. The tube shape is not necessary, because the outer contour of the adjustment rod can also serve as an X-ray marker.

The intervertebral plate 11 is about the size of the prosthesis which is later to be fitted. Its dimensions in the AP direction and LM direction (LM=lateral–medial, i.e. perpendicular to the median plane) are not significantly smaller than those of the intervertebral space. It should be at least 70% of the clear distance between the protrusions of the lower vertebral body, preferably at least 80%. Therefore, when it is driven into place, the intervertebral plate assumes a roughly central position. However, very often this position is still not precise enough. An X-ray apparatus having at least an AP beam path is thus used to check the central position of the intervertebral plate and its orientation with respect to the median plane, the position and direction of the outer surfaces of the adjustment rod 32 being critical here. They form the X-ray marker of the instrument for this check. For this purpose, the adjustment rod is made radiopaque, for example of metal. A lateral beam path can also be used to check whether the intervertebral plate has the correct depth setting in the AP direction. In this case, the X-ray marker is formed by those edges of the intervertebral plate which extend in the LM direction, or by a special marker such as the bore 13 in FIG. 1. However, the depth setting of the intervertebral plate is less important for the positioning of the prosthesis.

The intervertebral plate is secured in the intervertebral space by the tensioning of the natural ligaments. Its height corresponds to that of the prosthesis to be implanted. If prostheses of different sizes are available, corresponding intervertebral plates are also included in the instrument set.

The adjustment rod 32 is used for adjusting (positioning) the guide device 34. In FIGS. 8 and 9 it will be seen that the latter has a bore 35 with a square cross section which matches the portion 31 of the adjustment rod 32. This part of the guide device forms a hub by which it is held on the adjustment rod. It also comprises a bore 36 of round cross section parallel to the bore 35. This bore 36 serves as a drill gauge or more generally for guiding work tools. When the guide device 34 is pushed onto the portion 31 of the adjustment rod, it can assume the position shown in FIG. 7, in which the axis 37 defined by the bore 36 is aimed at the center of the upper vertebral body 2, and a position turned 180° from this, in which the axis 38 defined by the bore 36 is aimed at the center of the lower vertebral body. The axes 37 and 38 lie in the same median plane as the adjustment rod 32. Instead of the square cross section in the portion 31, it is also possible to choose another noncircular shape which permits interaction in two 180° offset positions of the guide device 34.

The guide device 34 is thus used first for working one vertebra, and it is then turned through 180° in order to work the other vertebra.

This work involves first making a hole in a vertebra by means of a drill 39 whose shaft is designed to match the bore 36, into which hole a screw pin 41 is then introduced by means of the screwdriver 40 whose shaft likewise matches the bore 36. The pin 41 fits exactly into a bore provided in the screwdriver 40, and this ensures that it is screwed into the respective vertebra flush with the screwdriver 40 and thus also flush with the axes 37, 38. After this has been done on both vertebrae, the picture shown in FIG. 13 is reached. By virtue of the guide device and its adjustment by the adjustment instrument, the screw pins 41 protrude ventrally from both vertebrae 2 exactly in the median plane and parallel to one another.

A distraction instrument can now be applied to the pins 41, said instrument having two arms 42, each of them with a receiving part 43 for the pins 41, and the arms 42 can be positioned on an instrument body 44 and distracted parallel to one another in arrow direction 45.

Such instruments are known and therefore do not need to be described here. With the aid of this instrument, the vertebrae 2 can, if necessary, be distracted slightly further so that the intervertebral plate 11 can be removed. If so desired, the intervertebral space can be worked in the state in which the vertebrae are held by the instrument 42 to 44 and the pins 41, in order to prepare to receive the intervertebral prosthesis. Finally, the latter is itself fitted into the intervertebral space and obtains its final position when the distraction of the vertebrae 2 with the instrument 42 to 44 is reversed.

The instrument set also comprises a collection of rasps which are used to prepare the surface shape of the vertebrae for receiving the prosthesis. These are shown in FIGS. 15 through 21. The examples shown are indicated for the illustrative embodiment of the prosthesis shown in FIGS. 22 and 23. It has an oval to rectangular contour designed to extensively utilize the area of the intervertebral space. It is so flat that it can be fitted without deep milling of the cover plates of the vertebral bodies. It has outer surfaces facing the cover plates of the vertebral bodies, these outer surfaces being approximately level and serrated in their largest part 50. Their dorsolateral corners 51 are beveled so that the surface in these areas is set back from the plane of the surface part 50.

This shape is prepared in the intervertebral space using a collection of rasps 52, 53 and 54 which are shown in FIGS. 15 through 20. FIG. 21 shows the graded sizes of the rasps. The smallest rasp 52 is first pushed into the intervertebral space, using a handpiece (not shown), in order to open up the access. This is followed by rasp 53 which has a trapezoid shape, roughly corresponding to the trapezoid shape of the level surface portion of the prosthesis surface. Finally, rasp 54 shapes the intervertebral space substantially to the shape of the prosthesis to be fitted. The height of the rasps is the same as that of the prosthesis.

All the rasps are designed without teeth in those surfaces corresponding to the level part of the prosthesis 50. This means that they effect only a slight abrasion with their front edge 55.

What is claimed is:

1. A method for fitting an intervertebral prosthesis into an intervertebral space between two vertebral bodies, comprising:

removing an intervertebral disk, positioning and securing an intervertebral plate of an adjustment instrument in the intervertebral space, sliding a hub of a guide device onto an adjustment rod projecting from the intervertebral plate in such a way that the guide device defines two guide axes made by through holes in a median plane above and below the adjustment rod and parallel thereto, introducing two pins into the vertebral bodies in the direction of the guide axes, thereafter, connecting a distraction forceps to the pins so that they are held parallel to one another, removing the guide device from the adjustment rod, setting a spacing of the intervertebral bodies, removing the adjustment rod, and working the intervertebral space as desired, thereby fitting the intervertebral prosthesis.

* * * * *

UNITED STATES PATENT AND TRADEMARK OFFICE
CERTIFICATE OF CORRECTION

PATENT NO. : 7,527,629 B2 Page 1 of 1
APPLICATION NO. : 10/731432
DATED : May 5, 2009
INVENTOR(S) : Helmut D. Link et al.

It is certified that error appears in the above-identified patent and that said Letters Patent is hereby corrected as shown below:

On the title page:

Under Section (30), "Foreign Application Priority Data," please replace "02005629" with --02005629.7--.

Column 1, line 8, please replace "European Application No. 02 005 628.7" with --European Application No. 02 005 629.7--.

Column 4, line 36, please replace "1800" with --180°--.

Signed and Sealed this

First Day of September, 2009

David J. Kappos
*Director of the United States Patent and Trademark Office*